United States Patent
Santora et al.

(10) Patent No.: US 6,524,594 B1
(45) Date of Patent: Feb. 25, 2003

(54) FOAMING OIL GEL COMPOSITIONS

(75) Inventors: Delores M. Santora, Somerville, NJ (US); John Hopkins, Chieveley (GB); Laura J. McCulloch, Kings Somborne (GB)

(73) Assignee: Johnson & Johnson Consumer Companies, Inc., Skillman, NJ (US)

(*) Notice: Subject to any disclaimer, the term of this patent is extended or adjusted under 35 U.S.C. 154(b) by 0 days.

(21) Appl. No.: 09/579,737

(22) Filed: May 26, 2000

Related U.S. Application Data

(60) Provisional application No. 60/140,605, filed on Jun. 23, 1999.

(51) Int. Cl.⁷ ............................. A61K 7/00; A61K 7/48; A61K 7/50
(52) U.S. Cl. ..................... 424/401; 424/78.03; 424/59; 510/475; 510/119; 510/120; 510/121
(58) Field of Search ................................ 510/475, 121, 510/119, 120; 424/401, 78.03, 59

(56) References Cited

U.S. PATENT DOCUMENTS

| | | |
|---|---|---|
| 4,215,064 A | 7/1980 | Lindemann et al. |
| 4,233,192 A | 11/1980 | Lindemann et al. |
| 4,372,869 A | 2/1983 | Lindemann et al. |
| 4,380,637 A | 4/1983 | Lindemann et al. |
| 4,382,036 A | 5/1983 | Lindemann et al. |
| 4,617,414 A | 10/1986 | Lukenbach et al. |
| 4,707,293 A | 11/1987 | Ferro |
| 5,221,534 A | 6/1993 | DesLauriers et al. |
| 5,804,539 A | 9/1998 | Gordon et al. |
| 5,817,609 A | 10/1998 | He et al. |
| 5,888,492 A | 3/1999 | Starch |
| 6,013,270 A * | 1/2000 | Hargraves et al. ........... 424/401 |
| 6,046,145 A * | 4/2000 | Santora et al. .............. 510/121 |
| 6,090,773 A * | 7/2000 | Lukenbach et al. ......... 510/475 |

FOREIGN PATENT DOCUMENTS

| | | |
|---|---|---|
| DE | 4424210 A1 | 8/1997 |
| WO | WO 97/26860 | 7/1997 |

OTHER PUBLICATIONS

European Search Report dated Jul. 27, 2001 for European Patent Application No. EP 00 30 5281.
U.S patent application Ser. No. 09/762,177 (J&J 1755).

* cited by examiner

*Primary Examiner*—Jose' G. Dees
*Assistant Examiner*—M. Haghighatian
(74) *Attorney, Agent, or Firm*—Erin M. Harriman

(57) ABSTRACT

A gelled oil composition containing an emulsifier, a gelling agent, an oil, and a surfactant which, when applied to the skin in the presence of water, produces a significant amount of foam. After the composition is rinsed from the skin, a non-greasy, oil residue is left thereon.

34 Claims, 1 Drawing Sheet

→ Ex. 45 (Ex. 7)   → Ex. 46 (Ex. 17)   → Ex. 47 (Ex. 14)   → Eucerin

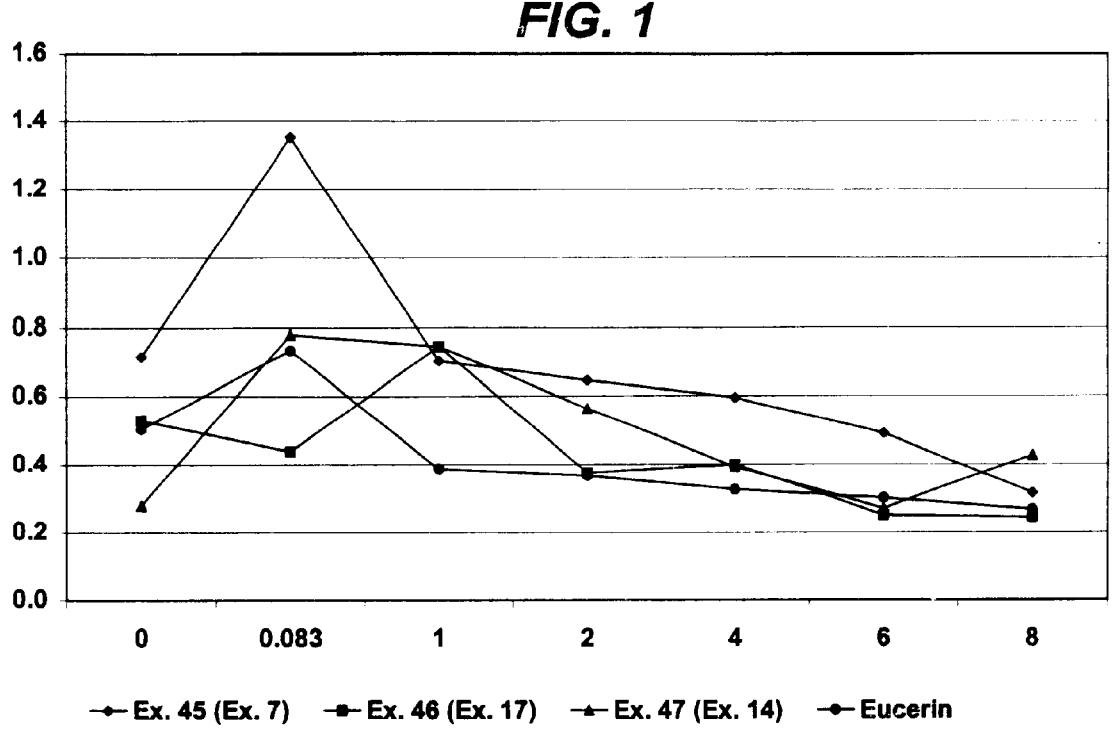

FOAMING OIL GEL COMPOSITIONS

This application claims benefit of No. 60/140,605 filed Jun. 23, 1999.

BACKGROUND OF THE INVENTION

1. Field of the Invention

This invention relates to gelled oil skin cleansing compositions, and to uses thereof. These compositions are not only effective, foaming cleansers, but they also leave a light, moisturizing feel to the skin after rinsing.

2. Description of the Prior Art

Cleansing the skin results, irrespective of the surfactants added, in swelling of the horny layers, with water-soluble constituents of dirt being washed off and substances endogenous to the skin being washed out. During this process, naturally occurring skin fats are also dissolved and removed, making it necessary to replenish the skin with these or subsidiary protective factors.

For this purpose, oil preparations are used as bath or shower preparations in the art. Typically, these preparations are provided as single-phase systems which, on contact with water, form an emulsion or a full solubilizate as opposed to dividing out into two phases. As a result of the formation of an emulsion, the skin is, during the cleansing operation, better cared for with the preferred oils than in two-phase systems.

Surfactant-containing oil preparations for use as cosmetic or dermatological shower oils are well-known in the art. For example, DE 4424210 C2 uses a composition containing at most 55 percent of surfactants comprised of various anionic and nonionic surfactants as well as at least 45 percent of a selection of oil components, with triglycerides being particularly preferred.

DE 19835239.5 also provides for a single-phase foaming oil composition that is non-irritative to the skin, mucosa, and eyes comprised of an anionic surfactant, a zwitterionic surfactant, or mixture thereof; a nonionic surfactant; an alkyl phosphate; and an oil component wherein the proportion of surfactant is from 15 percent to 50 percent and that of the oil component is from 50 percent to 85 percent.

U.S. Pat. No. 4,707,293, which uses a composition consisting essentially of: a) an animal, vegetable, mineral or synthetic oil; and b) from 2 percent to 20 percent of a mixture of a saccharose ester and at least one other emulsifying agent, claims to provide an effective cleanser that also leaves a protecting lipid layer on the skin.

Disadvantageously, many of the known surfactant-containing preparations often produce little to no foam, fail to leave a perceived amount of moisturizing residue on the skin, and/or are not significantly stable in a gelled form, a preferred mode of use for users of these products.

When formulating an oil preparation, particular care should be taken when it is used by people who suffer from diseases such as atopic eczema as well as those people whose skin requires special care, thus, for example, as a result of damage caused by the environment, irritation, light damage, and aging skin.

It would be desirable to have an effective, non-irritating cleansing composition that not only was stable in the preferred gel form, but also, after rinsing, left a non-greasy, moisturizing residue on the skin.

SUMMARY OF THE INVENTION

In accordance with this invention, there is provided a gelled detergent composition comprising:

a) a surfactant portion comprising at least one ionic surfactant;

b) an oil;

c) a gelling agent; and d) a nonionic emulsifier.

Another embodiment of the present invention is directed to a method for producing a gelled detergent composition comprising:

a) combining a gelling agent with a nonionic emulsifier to form a first mixture;

b) adding a surfactant to the first mixture to form a second mixture;

c) adding the second mixture to a third mixture comprised of an oil.

When the gelled composition of the present invention is applied to the skin in the presence of water, the composition produces a cleansing foam. When the product is rinsed off of the skin, a light oil residue remains on the skin, which provides the user with a moisturized "after-feel."

BRIEF DESCRIPTION OF THE DRAWINGS

The above and other aspects and novel features of the present invention will become apparent from the following detailed description of the preferred embodiments, as illustrated in the accompanying figures showing the improved moisturization imparted by using the method and composition of the present invention, wherein:

FIG. 1 is a graph of the degree of absorptivity of the mineral oil band versus time (hours) as determined by Fourier Transmittance Infrared ("FTIR") analysis.

DETAILED DESCRIPTION OF PREFERRED EMBODIMENTS

In one embodiment of the present invention, the gelled composition may suitably comprise, consist of, or consist essentially of, based upon the total weight of the composition, a) from about 10 percent to about 20 percent, and preferably from about 12 percent to about 17 percent of a surfactant portion comprising at least one ionic surfactant; b) from about 50 percent to about 90 percent, and preferably from about 60 percent to about 70 percent of an oil; c) from about 3 percent to about 10 percent, and preferably from about 3.5 percent to about 5.5 percent of a gelling agent; and d) from about 2.5 percent to about 20 percent, and preferably from about 3 percent to about 7 percent a nonionic emulsifier.

The first component in the composition of the present invention is a surfactant portion comprising at least one ionic surfactant such as an amphoteric, anionic, or nonionic surfactant. Examples of such suitable surfactants may be found in, for example, International Application No. US97/01196, which is incorporated herein by reference. As used herein, the term "amphoteric" shall mean: 1) molecules that contain both acidic and basic sites such as, for example, an amino acid containing both amino (basic) and acid (e.g., carboxylic acid, acidic) functional groups; or, 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Commercially available amphoteric surfactants are suitable for use in the present invention and include, but are not limited to amphocarboxylates; alkyl betaines, wherein the fatty alkyl group has rom about 12 carbon atoms to about 18 carbon atoms, and preferably from about 12 carbon atoms to about 14 carbon atoms; amidoalkyl betaines wherein the fatty alkyl group has from about 12 carbon atoms to about 18 carbon atoms, and preferably from about 12 carbon atoms to about 14 carbon atoms; amidoalkyl sultaines wherein the fatty alkyl group has from about 12 carbon atoms to about 18 carbon atoms, and preferably from about 12 carbon atoms to about 14 carbon atoms; amphophosphates; phosphobetaines; pyrophosphobetaines; carboxyalkyl alkyl polyamines wherein the first alkyl group of the carboxyalky moiety has from about 1 carbon atom to about 2 carbon atoms, and the second alkyl group has from about 12 carbon atoms to about 18 carbon atoms, and preferably from about 12 carbon atoms to about 14 carbon atoms and mixtures thereof.

Examples of suitable amphocarboxylate compounds include those of the formula I.:

A—CONH(CH$_2$)$_x$N$^+$R$_5$R$_6$R$_7$     I.

wherein
  A is an alkyl or alkenyl group having from about 7 to about 21, and preferably from about 10 to about 16 carbon atoms;
  x is an integer of from about 2 to about 6;
  R$_5$ is hydrogen or a carboxyalkyl group containing from about 2 to about 3 carbon atoms, and preferably is hydrogen;
  R$_6$ is a hydroxyalkyl group containing from about 2 to about 3 carbon atoms or is a group of the formula II.:

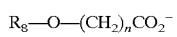

R$_8$—O—(CH$_2$)$_n$CO$_2^-$     II.

wherein
    R$_8$ is an alkylene group having from about 2 to about 3 carbon atoms and n is 1 or 2; and
    R$_7$ is a carboxyalkyl group containing from about 2 to about 3 carbon atoms;
The amphocarboxylate compound may be an imidazoline surfactant, and more preferably a disodium lauroamphodiacetate, which is commercially available from Mona Chemical Company of Paterson, N.J. under the tradename, "Monateric 949J."

Examples of suitable alkyl betaines include those compounds of the formula III:

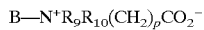

B—N$^+$R$_9$R$_{10}$(CH$_2$)$_p$CO$_2^-$     III wherein
  B is an alkyl or alkenyl group having from about 8 to about 22, and preferably from about 8 to about 16 carbon atoms;
  R$_9$ and R$_{10}$ are each independently an alkyl or hydroxyalkyl group having from about 1 to about 4 carbon atoms; and
  p is 1 or 2.
One betaine suitable for use in the present invention is lauryl betaine, available commercially from Albright & Wilson, Ltd. of West Midlands, United Kingdom as "Empigen BB/J."

Examples of suitable amidoalkyl betaines include those compounds of the formula IV:

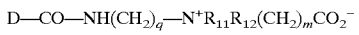

D—CO—NH(CH$_2$)$_q$—N$^+$R$_{11}$R$_{12}$(CH$_2$)$_m$CO$_2^-$     IV wherein
  D is an alkyl or alkenyl group having from about 7 to about 21, and preferably from about 7 to about 15 carbon atoms;
  R$_{11}$ and R$_{12}$ are each independently an alkyl or hydroxyalkylgroup having from about 1 to about 4 carbon atoms;
  q is an integer from about 2 to about 6; and m is 1 or 2.
A preferred amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula V.

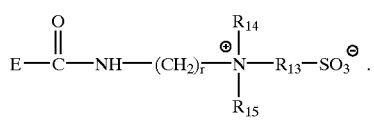

$$E-\overset{O}{\underset{}{\overset{\|}{C}}}-NH-(CH_2)_r-\overset{R_{14}}{\underset{R_{15}}{\overset{\oplus}{N}}}-R_{13}-SO_3^\ominus \quad . \quad V$$

wherein
  E is an alkyl or alkenyl group having from about 7 to about 21, and preferably from about 7 to about 15 carbon atoms;
  R$_{14}$ and R$_{15}$ are each independently an alkyl, or hydroxyalkyl group having from about 1 to about 4 carbon atoms;
  r is an integer from about 2 to about 6; and
  R$_{13}$ is an alkylene or hydroxyalkylene group having from about 2 to about 3 carbon atoms;
One suitable amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula VI:

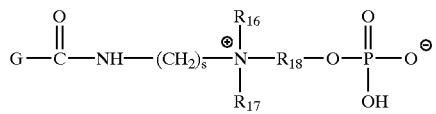

$$G-\overset{O}{\underset{}{\overset{\|}{C}}}-NH-(CH_2)_s-\overset{R_{16}}{\underset{R_{17}}{\overset{\oplus}{N}}}-R_{18}-O-\overset{O}{\underset{OH}{\overset{\|}{P}}}-O^\ominus \quad VI$$

wherein
  G is an alkyl or alkenyl group having about 7 to about 21, and preferably from about 7 to about 15 carbon atoms;
  s is an integer from about 2 to about 6;
  R$_{16}$ is hydrogen or a carboxyalkyl group containing from about 2 to about 3 carbon atoms;
  R$_{17}$ is a hydroxyalkyl group containing from about 2 to about 3 carbon atoms or a group of the formula VII:

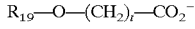

R$_{19}$—O—(CH$_2$)$_t$—CO$_2^-$     VII wherein
    R$_{19}$ is an alkylene or hydroxyalkylene group having from about 2 to about 3 carbon atoms and
    t is 1 or 2; and
  R$_{18}$ is an alkylene or hydroxyalkylene group having from about 2 to about 3 carbon atoms.

Suitable amphophosphate compounds include laurylamphosphates such as sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Phosphobetaines are also known as alkyl amido propyl phosphobetaines, wherein the alkyl group may contain from about 12 carbon atoms to about 18 carbon atoms, and preferably from about 12 carbon atoms to about 14 carbon atoms. Examples of suitable phosphobetaines include those compounds of the formula VIII:

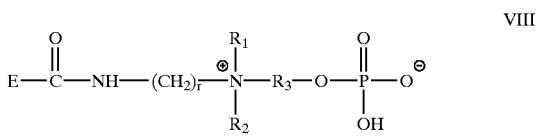

VIII wherein E, r, $R_1$, $R_2$ and $R_3$, are as defined above. The phosphobetaine compounds include those disclosed in U.S. Pat. Nos. 4,215,064, 4,617,414, and 4,233,192, which are all incorporated herein by reference. One example of a suitable phosphobetaine is cocoamidopropylphosphobetaine.

Pyrophosphobetaines are also known as alkyl amido pyrophosphobetaines, wherein the alkyl group may contain from about 12 carbon atoms to about 18 carbon atoms, and preferably from about 12 carbon atoms to about 14 carbon atoms. Examples of suitable pyrophosphobetaines include those compounds of the formula IX:

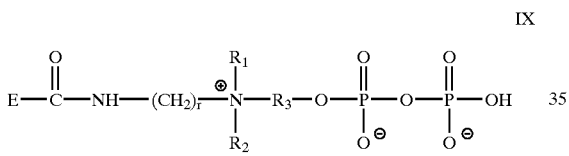

IX wherein E, r, $R_1$, $R_2$ and $R_3$, are as defined above. The pyrophosphobetaine compounds include those disclosed in U.S. Pat. Nos. 4,382,036, 4,372,869, and 4,617,414, which are all incorporated herein by reference. One example of a suitable pyrophosphobetaine includes lauric/myristic pyrophosphobetaine.

Examples of suitable carboxyalkyl alkylpolyamines include those of the formula X:

X wherein
  I is an alkyl or alkenyl group containing from about 8 to about 22, and preferably from about 8 to about 16 carbon atoms;
  $R_{22}$ is a carboxyalkyl group having from about 2 to about 3 carbon atoms;
  $R_{21}$ is an alkylene group having from about 2 to about 3 carbon atoms and
  u is an integer from about 1 to about 4.

One suitable carboxyalkyl alkyl polyamine is sodium carboxymethyl coco polypropylamine, available commercially from Akzo Nobel Surface Chemistry under the tradename, "Ampholak 7CX/C."

In a preferred embodiment, the amphoteric surfactant portion of the compositions is comprised of an amidoalkyl betaine, an amidoalkyl sultane, and mixtures thereof, wherein the alkyl group contains from about 8 to about 20 carbon atoms, and more preferably cocamidopropyl betaine, cocamidopropyl sultaine, and mixtures thereof.

Examples of suitable anionic surfactants include the anionic surfactants selected from the following classes of surfactants:

an alkyl sulfate of the formula XI

XI;

an alkyl ether sulfate of the formula XII

XII;

an alkyl monoglyceryl ether sulfate of the formula XIII

XIII an alkyl monoglyceride sulfate of the formula XIV

XIV.

an alkyl monoglyceride sulfonate of the formula XV

XV.

an alkyl sulfonate of the formula XVI.

XVI.

an alkylaryl sulfonate of the formula XVII.

XVII.

an alkyl sulfosuccinate of the formula XIX.:

XIX.

an alkyl ether sulfosuccinate of the formula XX.:

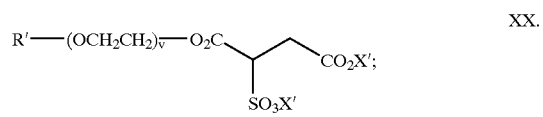

XX.

an alkyl sulfosuccinamate of the formula XXI.:

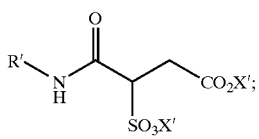
XXI.

an alkyl amidosulfosuccinate of the formula XXII.:

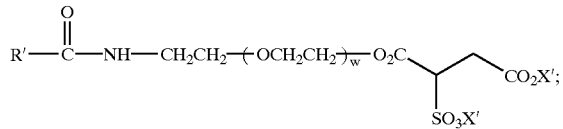
XXII an alkyl carboxylate of the formula XXIII:

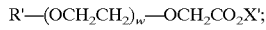
XXIII an alkyl amidoethercarboxylate of the formula XXIV:

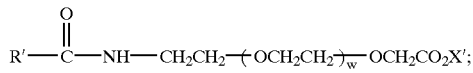
XXIV.

an alkyl succinate of the formula XXV.:

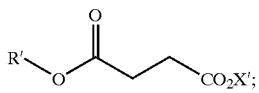
XXV.

a fatty acyl sarcosinate of the formula XXVI:

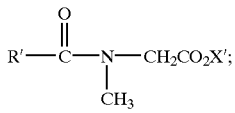
XXVI.

a fatty acyl amino acid of the formula XXVII:

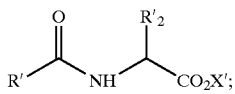
XXVII.

a fatty acyl taurate of the formula XXVIII.:

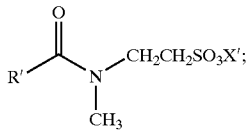
XXVIII.

a fatty alkyl sulfoacetate of the formula XXIX.:

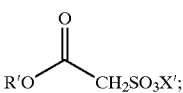
XXIX.

an alkyl phosphate of the formula XXX.:

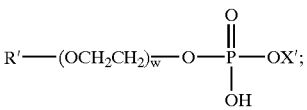
XXX.

wherein
  R' is an alkyl group having from about 7 to about 22, and preferably from about 7 to about 16 carbon atoms,
  $R'_1$ is an alkyl group having from about 1 to about 18, and preferably from about 8 to about 14 carbon atoms,
  $R'_2$ is a substituent of a natural or synthetic I-amino acid,
  X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
  v is an integer from 1 to 6;
  w is an integer from 0 to 20;
and mixtures thereof.

In a preferred embodiment using the above-mentioned anionic surfactants, the alkyl group has from about 6 carbon atoms to about 16 carbon atoms, the aryl group has 6 carbon atoms, and the acyl group has from about 12 carbon atoms to about 18 carbon atoms, and more preferably the anionic surfactant is comprised of sodium alkyl sulfosuccinate, wherein the alkyl group has from about 14 to about 16 carbon atoms, sodium cocoyl isethionate, cocamidopropyl MEA sulfosuccinate, sodium lauryl sulfate, and mixtures thereof, with sodium C14–C16 olefin sulfosuccinate being most preferred.

Suitable nonionic surfactants include alkyl polyglucosides wherein the alkyl group has from about 8 carbon atoms to about 16 carbon atoms, and preferably from about 10 carbon atoms to about 16 carbon atoms, e.g. decyl glucoside; cocoamidopropyl amine oxides; and mixtures thereof.

Preferably the surfactant portion contains, based upon the total weight of the surfactant portion, from about 20 percent to about 70 percent, and preferably from about 45 percent to about 55 percent of an amphoteric surfactant, and from about 20 percent to about 70 percent, and preferably from about 45 percent to about 55 percent of an anionic surfactant.

The second component of the composition of the present invention is an oil, which may be either a vegetable oil, a hydrocarbon oil, or mixtures thereof. Preferably the oil has an iodine value of less than about 80 percent, and preferably less than about 85 percent.

Examples of suitable hydrocarbon oils nonexclusively include mineral oil; hydrogenated polyisobutylene; poly-alpha olefins wherein the olefins have from about 20 carbon atoms to about 40 carbon atoms such as polydecene; isododecane; isohexadecane; isoeicosane; and mixtures thereof with mineral oil being preferred.

Examples of suitable vegetable oils nonexclusively include vegetable squalane oil, coconut oil, palm kernel oil, soybean oil, macadamia nut oil, avocado oil, safflower oil, with squalane oil, coconut oil, palm kernel oil, and mixtures thereof, with squalane oil being preferred.

The third component of the present invention is a gelling agent selected from dextrin myristate; dextrin palmitate; a blend of at least two different polymer members selected from the group consisting of diblock copolymers, triblock copolymers, radial block copolymers and multiblock copolymers; or a mixture thereof.

A preferred gelling agent is a polymeric blend comprised of, based upon the total weight of the blend, from about 5 percent to about 95 percent of at least one diblock copolymer or at least one triblock copolymer, wherein the diblock and triblock polymers are comprised of segments of oil-insoluble styrene monomer units and oil-soluble rubber monomer units, e.g. ethylene, propylene, butylene. More specifically, such gelling agents are in the form of a polymeric/oil blend and are comprised of, based upon the weight of the total polymeric/oil blend, from about 1 percent to about 20 percent of a polymeric portion comprised of diblock polymers and triblock polymers and about 80 percent to about 99 percent of a hydrocarbon oil. Preferably, the polymeric portion is comprised of, based upon the total weight of the polymeric portion, from about 10 percent to about 90 percent of diblock polymer and from about 90 percent to about 10 percent of triblock polymer. Preferably, the diblock copolymers and triblock copolymers are present in a ratio of from about 2:1 to about 1:3. Preferred polymeric blends include styrene-ethylene/propylene block copolymers and styrene-ethylene/butylene-styrene block copolymers available from Shell Chemical Company under the tradenames, "KRATON G1702" and "KRATON G1650," respectively. While the viscosity of the polymeric/oil blend will depend upon the ratios of the diblock polymers and the triblock polymers contained therein, preferably the polymeric/oil blend will have an average viscosity of from about 20,000 cps to about 160,000 cps, and more preferably from about 40,000 cps to about 60,000 cps. Such gelling agents are disclosed in U.S. Pat. No. 5,221,534, which is incorporated by reference herein in its entirety, and are commercially available from Pennzoil Products Company under the tradename, "Geahlene."

The fourth component of the composition of the present invention is an emulsifier. Preferably, the emulsifer possesses an Hydrophile-Lipophile Balance ("HLB") that is below about 10. Examples of suitable emulsifiers nonexclusively include glyceryl esters such as glyceryl oleate; sorbitan esters such as sorbitan oleate or sorbitan stearate; methyl glucose esters such as methyl glucose sesquistearate and methyl glucose dioleate; polyethylene glycol ethers of alkyl alcohols having the formula XXXI.:

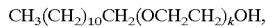   XXXI.

wherein k is an integer from about 1 to about 20, and preferably from about 1 to about 10, and mixtures thereof, with laureth-3, laureth-4, and mixtures thereof being preferred.

In a preferred embodiment, the gelled composition may be essentially water-free. By "essentially water free," it is meant that the gelled composition comprises, based upon the total weight of the gelled composition, no more than about 5 percent of water. More preferably, the composition comprises, based upon the total weight of the composition, no more than about 3 percent, and most preferably no more than about 2 percent of water or other suitable vehicle.

Optional ingredients that may be included in the composition of the present invention include various esters, ethoxylated alcohols, benefit agents, and mixtures thereof. Preferably, these optional ingredients are added to gelling agent of the composition of the present invention after the gelling agent is heated to a temperature to improve its flow and ease of mixing, i.e. from about 60° C. to about 95° C.

By "benefit agent," it is mean any active ingredient that is to be delivered into and/or onto the skin at a desired location, such as a cosmetic agent or a pharmaceutical agent. By "cosmetic agent," it is meant any ingredient that is appropriate for cosmetically treating, providing nutrients to, and/or conditioning the hair and/or skin via topical application. By "pharmaceutical agent," it is mean any drug that is either hydrophobic or hydrophilic in nature and appropriate for topical use. As used herein "medicament agents" include those agents capable of promoting recovery from injury and illness.

Examples of suitable benefit agents include, but are not limited to, fragrances, depigmentation agents; reflectants; thickening agents; detangling/wet combing agents; film forming polymers; humectants; amino acid agents; antimicrobial agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents, antihistamines; antiinfectives; inflammation inhibitors; anti-emetics; anticholinergics; vasoconstrictors; vasodilators; wound healing promoters; peptides, polypeptides and proteins; deodorants and antiperspirants; medicament agents; skin emollients and skin moisturizers; hair conditioners; hair softeners; hair moisturizers; vitamins; tanning agents; skin lightening agents; antifungals such as antifungals for foot preparations; depilating agents; shaving preparations; external analgesics; perfumes; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavoids; sensates; anti-oxidants; skin conditioners; hair lighteners; chelating agents; cell turnover enhancers; coloring agents; pigments; sunscreens and the like, and mixtures thereof. The amount of certain cleansing composition/delivery system compounds for the benefit agent purposes set forth below is in addition to the amount of the same compound that may be desired for use in the cleansing composition/delivery system therefor.

Examples of suitable reflectants nonexclusively include mica, alumina, calcium silicate, glycol dioleate, glycol distearate, silica, sodium magnesium fluorosilicate, and mixtures thereof.

Examples of suitable UV absorbers include benzophenone, bornelone, butyl paba, cinnamidopropyl trimethyl ammonium chloride, disodium distyrylbiphenyl disulfonate, paba, potassium methoxycinnamate, and mixtures thereof.

Commercially available thickening agents that are capable of imparting the appropriate viscosity to the conditioning shampoo compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of polyethylene glycol of formula XXXII.

   XXXII.

wherein z is an integer from about 3 to about 200; fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose;, hydroxyalkyl alkyl cellulose; and mixtures thereof. More specifically, suitable thickening agents nonexclusively include behenalkonium chloride; cetyl alcohol, quaternium 46, PG-hydroxyethyl cellulose, cocodimonium chloride, polyquaternium 6, polyquaternium 7, quaternium 18, PEG-18 glycerol oleate/cocoate, a mixture of acrylates/spirit 50 acrylate copolymer, laureth 3 and propylene glycol, which is commercially available from Goldschmidt under the tradename "Antil 208," a mixture of cocamidopropylbetaine and glyceryl laurate which is commercially available from Goldschmidt under the tradename, "Antil HS60," a mixture of propylene glycol, PEG 55, and propylene glycol oleate, which is commercially available from Goldschmidt under the tradename, "Antil 414 liquid," and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Suitable detangling/wet combing agents nonexclusively include dioleoylamidoethyl hydroxythylmonium methosulfate, di (soyoylethyl) hydroxyethylmonium methosulfate, hydroxyethyl behenamidopropyl dimonium chloride, olealkonium chloride, polyquaternium 47, stearalkonium chloride, tricetylmonium chloride, and mixtures thereof.

Suitable film forming polymers include those that, upon drying, produce a substantially continuous coating or film on the hair, skin, or nails. Nonexclusive examples of suitable film forming polymers include acrylamidopropyl trimonium chloride/acrylamide copolymer; corn starch/acrylamide/sodium acrylate copolymer; polyquaternium 10; polyquaternium 47; polyvinylmethyl/maleic anhydride copolymer; styrene/acrylates copolymers; and mixtures thereof.

Commercially available humectants which are capable of providing moisturization and conditioning properties to the cleansing composition are suitable for use in the present invention. The humectant is preferably present in an amount of from about 0 percent to about 10 percent, more preferably from about 0.5 percent to about 5 percent, and most preferably from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, pentylene glycol, dipropylene glycol, and mixtures thereof; 2) polyalkylene glycol of the formula XXXIII.:

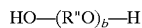

HO—(R"O)$_b$—H          XXXIII.

wherein R" is an alkylene group having from about 2 to about 4 carbon atoms and b is an integer of from about 1 to about 10, such as PEG 4; 3) polyethylene glycol ether of methyl glucose of formula XXXIV:

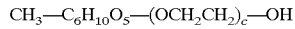

CH$_3$—C$_6$H$_{10}$O$_5$—(OCH$_2$CH$_2$)$_c$—OH          XXXIV.

wherein c is an integer from about 5 to about 25; 4) urea; 5) fructose; 6) glucose; 7) honey; 8) lactic acid; 9) maltose; 10) sodium glucuronate; and 11) mixtures thereof, with glycerine being the preferred humectant.

Suitable amino acid agents include amino acids derived from the hydrolysis of various proteins as well as the salts, esters, and acyl derivatives thereof. Examples of such amino acid agents nonexclusively include amphoteric amino acids such as alkylamido alkylamines, i.e. stearyl acetyl glutamate, capryloyl silk amino acid, caprylol collagen amino acids; capryloyl keratin amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, citrulline; lysine; silk amino acids, wheat amino acids; and mixtures thereof Suitable proteins include those polymers that have a long chain, i.e. at least about 10 carbon atoms, and a high molecular weight, i.e. at least about 1000, and are formed by self-condensation of amino acids. Nonexclusive examples of such proteins include collagen, deoxyribonuclease, iodized corn protein; keratin; milk protein; protease; serum protein; silk; sweet almond protein; wheat germ protein; wheat protein; wheat protein, alpha and beta helix of keratin proteins; hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Examples of suitable vitamins nonexclusively include vitamin B complex; including thiamine, nicotinic acid, biotin, pantothenic acid, choline, riboflavin, vitamin B6, vitamin B12, pyridoxine, inositol, carnitine; vitamins A,C, D,E,K and their derivatives such as vitamin A palmitate and pro-vitamins, e.g. (i.e. panthenol (pro vitamin B5) and panthenol triacetate) and mixtures thereof.

Examples of suitable antibacterial agents nonexclusively include bacitracin, erythromycin, neomycin, tetracycline, chlortetracycline, benzethonium chloride, phenol, and mixtures thereof.

Examples of suitable skin emollients and skin moisturizers nonexclusively include mineral oil, lanolin, vegetable oils, isostearyl isostearate, glyceryl laurate, methyl gluceth 10, methyl gluceth 20 chitosan, and mixtures thereof.

Examples of suitable hair conditioners nonexclusively include quaternized compounds such as behenamidopropyl PG-dimonium chloride, tricetylammonium chloride, dihydrogenated tallowamidoethyl hydroxyethylmonium methosulfate, and mixtures thereof as well as lipophilic compounds like cetyl alcohol, stearyl alcohol, hydrogenated polydecene, and mixtures thereof.

An example of a suitable hair softener nonexclusively includes silicone compounds, such as those that are either non-volatile or volatile and those that are water soluble or water insoluble. Examples of suitable silicones include organo-substituted polysiloxanes, which are either linear or cyclic polymers of monomeric silicone/oxygen monomers and which nonexclusively include cetyl dimethicone; cetyl triethylammonium dimethicone copolyol phthalate; cyclomethicone; dimethicone copolyol; dimethicone copolyol lactate; hydrolyzed soy protein/dimethicone copolyol acetate; silicone quaternium 13; stearalkonium dimethicone copolyol phthalate; stearamidopropyl dimethicone; and mixtures thereof.

Examples of suitable hair moisturizers nonexclusively include panthenyl ethyl ether, phytantriol, and mixtures thereof.

Examples of sunscreen agents nonexclusively include butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate o, red petrolatum, and mixtures thereof.

An example of a suitable tanning agent nonexclusively includes dihydroxyacetone.

Examples of skin lightening agents nonexclusively include hydroquinone, catechol and its derivatives, ascorbic acid and its derivatives, and mixtures thereof.

Examples of suitable insecticides (including insect repellents, anti-scabies and anti-lice treatments) nonexclusively include permethrin, pyrethrin, piperonyl butoxide, imidacloprid, N,N-diethyl toluamide, which refers to the material containing predominantly the meta isomer, i.e., N,N-diethyl-m-toluamide, which is also known as DEET; compounds of the formula XXXV.:

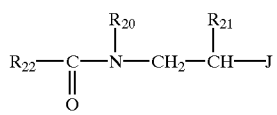

XXXV.

wherein
$R_{20}$ is a branched or unbranched alkyl group having about 1 to about 6 carbon atoms;
$R_{21}$ is H, methyl or ethyl;
$R_{22}$ is a branched or unbranched alkyl or alkoxy group having from about 1 to about 8 carbon atoms; and
J is a —CN or a —COOR$_{23}$ group, wherein
$R_{23}$ is a branched or unbranched alkyl group having from about 1 to about 6 carbon atoms,
natural or synthetic pyrethroids, whereby the natural pyrethroids are contained in pyrethrum, the extract of the ground flowers of *Chrysanthemum cinerariaefolium* or *C coccineum*; and mixtures thereof. Within the structure of Formula XXXV . . . are ethyl 3-(N-butylacetamido)propionate, wherein $R_{22}$ is a CH$_3$ group, $R_{20}$ is an n-butyl group, $R_{21}$ is H, K is COOR$_{23}$ and $R_{23}$ is ethyl, which is available commercially from Merck KGaA of Darmstadt, Germany under the name, "Insect Repellent 3535."

An example of an anti fungal for foot preparations nonexclusively includes tolnaftate.

Examples of suitable depilating agents nonexclusively include calcium thioglycolate, magnesium thioglycolate, potassium thioglycolate, strontium thioglycolate, and mixtures thereof.

Examples of suitable external analgesics and local anesthetics nonexclusively include benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Examples of suitable antiperspirants and deodorants nonexclusively include aluminium chlorohydrates, aluminium zirconium chlorohydrates, and mixtures thereof.

Examples of suitable counterirritants nonexclusively include camphor, menthol, methyl salicylate, peppermint and clove oils, ichtammol, and mixtures thereof.

An example of a suitable inflammation inhibitor nonexclusively includes hydrocortisone.

Examples of suitable hemorrhoidal products nonexclusively include the anesthetics such as benzocaine, pramoxine hydrochloride, and mixtures thereof; antiseptics such as benzethonium chloride; astringents such as zinc oxide, bismuth subgallate, balsam Peru, and mixtures thereof; skin protectants such as cod liver oil, vegetable oil, and mixtures thereof.

Examples of suitable make-up preparations nonexclusively include components for lipstick, rouge, blush, eye liner, eyeshadow powder, mascara, face powder, and mixtures thereof.

One preferred type of benefit agent includes those therapeutic components that are effective in the treatment of dandruff, seborrheic dermatitis, and psoriasis as well as the symptoms associated therewith. Examples of such suitable benefits agents nonexclusively include zinc pyrithione, shale oil and derivatives thereof such as sulfonated shale oil, selenium sulfide, sulfur; salicylic acid; coal tar; povidone-iodine, imidazoles such as ketoconazole, dichlorophenyl imidazolodioxalan, which is commercially available from Janssen Pharmaceutica, N.V., under the tradename, "Elubiol", clotrimazole, itraconazole, miconazole, climbazole, tioconazole, sulconazole, butoconazole, fluconazole, miconazolenitrite and any possible stereo isomers and derivatives thereof such as anthralin; piroctone olamine (Octopirox); selenium sulfide; ciclopirox olamine; anti-psoriasis agents such as vitamin D analogs, e.g. calcipotriol, calcitriol, and tacaleitrol; vitamin A analogs such as esters of vitamin A, e.g. vitamin A palmitate, retinoids, retinols, and retinoic acid; corticosteroids such as hydrocortisone, clobetasone, butyrate, clobetasol propionate and mixtures thereof.

Most preferred benefit agents nonexclusively include sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

The amount of benefit agent to be combined with the gelled composition may vary depending upon, for example, the resulting benefit desired and the sensitivity of the user to the benefit agent. Unless otherwise expressed herein, preferably the benefit agent is present in the gelled composition in an amount, based upon the total weight of the gelled composition, from about 0.001 percent to about 20 percent, and preferably from about 0.001 percent to about 10 percent, and more preferably from about 0.001 percent to about 5 percent.

The gelled composition of this invention are multi-phased, regardless of whether or not not water is incorporated, and preferably has a viscosity of from about 50,000 cps to about 150,000 cps, and preferably from about 60,000 cps to about 100,000 cps.

The composition of this invention may be applied to the desired area in the form of, for example, a lotion, cream, gel, soap, bath, mousse, tonic, or the like which is designed to be rinsed off within a given amount of time after application. Preferably, the gelled composition may be used to prepare a foaming oil preparation suitable for use in, for example, an oil bath, a shower preparation, a face-cleansing fluid, a make-up remover, or a body wash.

The composition of the present invention may be directly applied to the skin for cleansing, or preferably may be applied to the skin via a cleansing implement. Examples of suitable cleansing implements nonexclusively include brushes, sponges, foams, cloths, and poufs, with poufs being most preferred. Examples of suitable poufs are disclosed in, for example U.S. Pat. No. 5,804,539, which is incorporated herein by reference.

As the composition is applied to the skin, either with or without the aid of a cleansing implement, the oil component becomes emulsified and forms small droplets on the skin, while the surfactant simultaneously generates a significant amount of foam for cleansing. After the composition is rinsed-off, the user is left with a moisturized feeling on the skin that is less greasy than other known moisturizing cleansing products.

We have surprisingly found that the composition of the present invention advantageously offers the benefit of an oil treatment bath during the time that it takes the user to shower. In addition, the composition also advantageously deposits moisturizers to the skin during showering, which obviates the need for the user to apply a post-bathing moisturizer to the skin. Additionally, the composition is also effective in treating the symptoms of dry skin often associated with atopic dermatitis, xerosis, psoriatsis, winter itch, and other skin dermatoses.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

Examples 1–5

Preparation of Gel Formulations

The formulations prepared in Example 1 through Example 5 are set forth in Table A below:

TABLE A

| | Composition of Gel Formulations | | | | |
|---|---|---|---|---|---|
| | Composition (wt. %) | | | | |
| Component | Example 1 | Example 2 | Example 3 | Example 4 | Example 5 |
| Geahlene 500[1] | 79 | 75 | 70 | 65 | 60 |
| Laureth-3[4] | 5 | 5 | 5 | 5 | 5 |
| Isopropyl Palmitate[4] | 15 | 15 | 15 | 15 | 15 |
| Empigen BS-98[2] | 1 | 5 | 10 | 15 | 20 |
| Viscosity[3] | 72,400 | 88,000 | 97,360 | 109,840 | 125,440 |

[1] is a gelled mineral oil (and) hydrogenated butylene/ethylene Styrene copolymer and hydrogenated ethylene/propylene/styrene copolymer from the Penreco division of Pennzoil Products Company
[2] is cocamidopropyl betaine having a water content of 2.0% max., which is available from Albright & Wilson UK Ltd.
[3] Viscosity determined using a Model LVT Brookfield viscometer having a number T-E spindle at 1.5 rpm and at 25° C. for one minute.
[4] Available from Croda Surfactants, Ltd.

The formulations of Examples 1 through 5 were made as follows:

Isopropyl palmitate was charged to a vessel. To this was added laureth-3 with mixing at room temperature. Empigen BS-98 was then added slowly with continuous mixing until a homogeneous slurry was formed. The resultant slurry was added slowly with continued agitation to the Geahlene contained in a second vessel until the slurry was uniformly dispersed in the Geahlene.

Example 6

Evaluation of Foam Generation and "After Feel"

The formulations of Examples 1 through 5 were prepared in accordance with the procedure set forth in Examples 1–5, and then were evaluated for foam generation and skin feel after washing ("after-feel") as follows:

After about 5 ml of each respective formulation was dispensed into wet hands, the hands were then rubbed together for about 10 seconds and the volume of foam generated was qualitatively observed and recorded. The formulation was then rinsed from the hands, then the hands were patted dry with a paper towel. The hands were then qualitatively assessed for perceived residue left on the skin and the perceived "after feel" of the resultant moisturization residue. Results of these evaluations are summarized in Table B below:

TABLE B

| | Foam Generation and "After Feel" | | | |
|---|---|---|---|---|
| Formulation (Example) | Betaine Level | Foam Quality | After-feel | Other |
| 1 | 1.0% | No foam generated | Excessively greasy feel | |
| 2 | 5.0% | No foam generated | Excessively greasy feel | |
| 3 | 10% | Minimal foam generated | Soft, smooth feel with some greasy after-feel | |
| 4 | 15% | Acceptable amount of foam and good foam quality | Moisturized but not greasy feel | |
| 5 | 20% | Slightly better foam than 15% | Slightly less moisturized but not greasy feel | product becoming too thick |

This Example showed that as the surfactant level in the formulation product increased, the user's perception of greasiness/residue decreased, the amount and quality of the foam increased, and the viscosity of the product increased. This Example showed that an effective foaming cleanser with acceptable "after-feel" may be prepared by using a surfactant in an amount of, based upon the total weight of the composition, from about 10 percent to about 20 percent, and more preferably, from about 15 percent to about 20 percent.

Examples 7–25

Preparation of Gelled Formulations

The formulations set forth in Table C below were prepared in accordance with the procedure set forth in Examples 1–5, with the exception that the betaine component was substituted by the alternative surfactant systems described below in Table C.

TABLE C

| INGREDIENTS | TRADE NAME | Ex. 7 % W/W | Ex. 8 % W/W | Ex. 9 % W/W | Ex. 10 % W/W | Ex. 11 % W/W | Ex. 12 % W/W | Ex. 13 % W/W | Ex. 14 % W/W | Ex. 15 % W/W | Ex. 16 % W/W |
|---|---|---|---|---|---|---|---|---|---|---|---|
| gelled mineral oil & copolymers | Geahlene 500 | 64.40 | 78.40 | 74.40 | 69.40 | 59.40 | 64.90 | 64.90 | 64.90 | 64.90 | 64.90 |
| Cocoamidopropyl Dimethyl Betaine | Empigen BS 98 | 15.00 | 1.00 | 5.00 | 10.00 | 20.00 | | | | | 7.50 |
| Isopropyl Palmitate | Isopropyl Palmitate | 15.00 | 15.00 | 15.00 | 15.00 | 15.00 | 15.00 | 15.00 | 15.00 | 15.00 | 15.00 |
| Laureth-3 | Volpo L3 Special | 5.00 | 5.00 | 5.00 | 5.00 | 5.00 | 5.00 | 5.00 | 5.00 | 5.00 | 5.00 |
| Tocopherol Acetate (antioxidant) | Vitamin E Acetate | 0.10 | 0.10 | 0.10 | 0.10 | 0.10 | 0.10 | 0.10 | 0.10 | 0.10 | 0.10 |
| Sodium C14–16 Olefin Sulfosuccinate* | Bioterge AOS | | | | | | | | | 15.00 | |
| Sodium Cocoyl Isethionate** | Taurenol I-78 | | | | | | | | 15.00 | | |
| Cocamidopropyl MEA Sulfosuccinate*** | Makanate CMB-100 | | | | | | 20.00 | | | | |
| Disodium Lauryl Sulfosuccinate*** | Makanate LO-100 | | | | | | | | | | 15.00 |
| Sodium Lauryl Sulfate**** | Stepanol WA 100 | | | | | | | | | | 7.50 |
| Fragrance | Fragrance | 0.50 | 0.50 | 0.50 | 0.50 | 0.50 | | | | | |
| Light Mineral Oil***** | Drakeol 7 | | | | | | | | | | |
| Dextrin Palmitate****** | Rheopearl KL | | | | | | | | | | |

| INGREDIENTS | TRADE NAME | Ex. 17 % W/W | Ex. 18 % W/W | Ex. 19 % W/W | Ex. 20 % W/W | Ex. 21 % W/W | Ex. 22 % W/W | Ex. 23 % W/W | Ex. 24 % W/W | Ex. 25 % W/W |
|---|---|---|---|---|---|---|---|---|---|---|
| gelled mineral oil & copolymers | Geahlene 500 | 64.90 | 64.90 | 64.90 | 64.90 | 64.90 | | | | 64.90 |
| Cocoamidopropyl Dimethyl Betaine | Empigen BS 98 | | | | | | | | | |
| Isopropyl Betaine | Isopropyl Palmitate | 15.00 | 15.00 | 15.00 | 15.00 | 15.00 | | | | 15.00 |
| Laureth-3 | Volpo L3 Special | 5.00 | 5.00 | 5.00 | 5.00 | 5.00 | | | | 5.00 |
| Tocopherol Acetate (antioxidant) | Vitamin E Acetate | 0.10 | 0.10 | 0.10 | 0.10 | 0.10 | | | | 0.10 |
| Sodium C14–16 Olefin Sulfosuccinate* | Bioterge AOS | 7.50 | 11.00 | | | | 15.00 | | | 13.00 |
| Sodium Cocoyl Isethionate** | Taurenol I-78 | | | 7.50 | | | | 15.00 | | |
| Cocamidopropyl MEA Sulfosuccinate*** | Makanate CMB-100 | | | | 13.00 | | | | 13.00 | |
| Disodium Lauryl Sulfosuccinate*** | Makanate LO-100 | | | | | 7.50 | | | | |
| Sodium Lauryl Sulfate**** | Stepanol WA 100 | 7.50 | 4.00 | 7.50 | 2.00 | 7.50 | | | 2.00 | 2.00 |
| Fragrance | Fragrance | | | | | | | | | |
| Light Mineral Oil***** | Drakeol 7 | | | | | | 80.00 | 80.00 | 80.00 | |
| Dextrin Palmitate****** | Rheopearl KL | | | | | | 5.00 | 5.00 | 5.00 | |

*an anionic surfactant, available from Stepan Chemicals, Co.
**an anionic surfactant, available from FineTex, Inc.
***an anionic surfactant available from McIntyre Chemical Co.
****an anionic surfactant, available from Stepan Chemicals Co.
*****available from Penreco
******a gelling agent, available from Chiba Flour & Milling Co., Ltd.

Examples 26–44

Viscosity, Residue and Foam Generation

For each of the formulations set forth in Examples 7–25, the viscosity and the perceived amount of amount of residue left on skin was evaluated in accordance with the procedure set forth in Example 1–5 and Example 6, respectively. The amount of foam generation was also evaluated for most of these formulations in accordance with the procedure set forth in Example 6. The foam generated by these formulations was compared to the amount of foam generated by an "Oil of Olay Body Wash" that is commercially available from The Procter & Gamble Company. The results of the former two tests are set forth in Table D below, and the results of the latter test are set forth in Table E below.

TABLE D

Residue and Viscosity of Formulations of Example 7 (Example 26)–Example 25 (Example 44)

| | | Ex. (#) | | | | | | | | | | |
|---|---|---|---|---|---|---|---|---|---|---|---|---|
| | | Ex. 7/ Ex. 26 | Ex. 8/ Ex. 27 | Ex. 9/ Ex. 28 | Ex. 10/ Ex 29 | Ex. 11/ Ex 30 | Ex. 12/ Ex 31 | Ex. 13/ Ex 32 | Ex. 14/ Ex 33 | Ex. 15/ Ex 34 | Ex. 16/ Ex 35 | Ex. 17/ Ex 36 |
| RESIDUE* | | Yes | Yes | Yes | Yes | Yes | Yes | No | Yes | Yes | Yes | Yes |
| VISCOSITY** | Initial, cps | 109, 840 | 72, 400 | 88, 000 | 97, 360 | 125, 440 | 290, 800 | 104, 520 | 81, 120 | 104, 520 | 249, 600 | 82, 680 |
| | Present, cps | | | | | | | | 143, 520 | | | |
| | Parameters/Viscosity: | | | | | | | | | | | |
| | Reading | 35.205 | 23.205 | 28.205 | 31.205 | 40.205 | 90.00 | 33.50 | 26.00 | 33.50 | 80.00 | 26.50 |
| | Factor | 3120 | 3120 | 3120 | 3120 | 3120 | 3120.00 | 3120 | 3120 | 3120 | 3120 | 3120 |

| | | | Ex. (#) | | | | | | | |
|---|---|---|---|---|---|---|---|---|---|---|
| | | | Ex. 18/ Ex 37 | Ex. 19/ Ex 38 | Ex. 20/ Ex 39 | Ex. 21/ Ex 40 | Ex. 22/ Ex 41 | Ex. 23/ Ex 42 | Ex. 24/ Ex 43 | Ex. 25/ Ex 44 |
| | RESIDUE* | | No | Yes | Yes | Yes | No | No | No | Yes |
| | VISCOSITY** | Initial, cps | 87, 360 | 84, 240 | 137, 280 | 90, 480 | 37, 440 | 37, 440 | 35, 880 | 106, 080 |
| | | Present, cps | | | | too thick | 49, 920 | 43, 680 | 40, 560 | |
| | | Parameters/Viscosity: | | | | | | | | |
| | | Reading | 31.205 | 27.00 | 44.00 | 29.00 | 12/16 | 12/14 | 11.5/13 | 34.00 |
| | | Factor | 3120 | 3120 | 3120 | 3120 | 3120 | 3120 | 3120 | 3120 |

*Residue left on skin after handwashing
**Viscosity was measured using a Brookfield LVT viscometer with a T-E spindle at a speed of 1.5 rpm, a temperature of 25° C., for 1 minute.

TABLE E

Foam Generation

| Product | Example # | Flash Foam | Amt. Foam | Foam Quality | Foam Stab. | Total |
|---|---|---|---|---|---|---|
| Geahlene Base, no surfactant | 31 | 1 | 1 | 2 | 1 (R) | 5 |
| G. Base, 15% Empigen, Fragrance | 26 | 3 | 5 | 5 | 5 (R) | 18 |
| G. Base, 15% Taurenol | 32 | 3 | 4 | 4 | 5 (NR) | 16 |
| G. Base, 15% Mackinate LO-100 | 34 | 2 | 3 | 3.5 | 2 (SR) | 10.5 |
| G. Base, 7.5/7.5 Bioterge/SLS | 36 | 5 | 4 | 4 | 4 (SR) | 17 |
| G. Base, 7.5/7.5 Empigen/SLS | 35 | 4 | 5 | 5 | 4.5 (SR) | 18.5 |
| G. Base, 7.5/7.5 Taurenol/SLS | 38 | 4 | 5 | 5 | 4 (SR) | 18 |
| G. Base, 13/2 Mackinate CMB-100/SLS | 39 | 3 | 4 | 4 | 2 (SR) | 13 |
| G. Base, 11/4 Bioterge/SLS | 37 | 4.5 | 5 | 5 | 4.5 (NR) | 19 |
| G. Base, 7.5/7.5 Mackinate LO-100/SLS | 40 | 4 | 4.5 | 5 | 4 (SR) | 17.5 |
| 5% Dex. Palm. Base, 15% Bioterge | 41 | 1 | 1 | 2 | 1 (NR) | 5 |
| 5% Dex. Palm. Base, 15% Taurenol | 42 | 2 | 3 | 3 | 4 (NR) | 12 |
| 5% Dex. Palm. Base, 13/2 Mack CMB/SLS | 43 | 1 | 2 | 2 | 3.5 (NR) | 8.5 |
| G. Base, 13/2 Bioterge/SLS | 44 | 4 | 4.5 | 4 | 4 (SR) | 16.5 |
| Oil of Olay Body Wash* | N/A | 5 | 5.5 | 5 | 4.75 (NR) | 20.25 |

Scale:
1-Poor
2-Fair
3-Average
4-Very Good
5-Excellent
Note:
(R)-Residue
(SR)-Slight Residue
(SR dried)-Slight Residue but drier feeling
(NR)-No Residue feeling left on skin These Examples further showed that as the amount of surfactant in the formulation was increased, the perceived level of residue on the skin was decreased while the amount of foam generated was increased.

These Examples further showed that the formulations containing sulfosuccinates, preferably in amounts less than about 15 weight percent, produced an acceptable amount of foam that is comparable to the amount of foam produced by the commercial body wash. However, unlike the commercial bodywash, only the formulations of the present invention were able to produce an acceptable amount of foam as well as leave an aesthetically acceptable perceived residue on the skin.

Examples 45–48

Fourier Transmittance Infrared Spectroscopy

After the forearms of 10 adults between the ages of about 25 to about 60 years were washed with a commercial soap then dried, a baseline spectrum of these forearms was obtained on a Nicolet model AVATAR 360 FTIR spectometer with the Spectra-Tech Skin Analyzers ATR accessory.

After moistening a forearm of each participant with warm water having a temperature of approximately 38° C., approximately 10.00 ml (10 g) of a formulation was applied to a pouf. The following formulations were used independently: Example 7, Example 14, Example 17, and the formulation of "Eucerin Shower Therapy" wash commercially available from Biersdorf Inc., under the tradename, "EUCERIN.". For each participant, this formulation was then applied to one forearm via the pouf. This procedure was repeated on the other forearm of each respective participant, but using a different formulation applied on another pouf.

The respective areas were washed with the pouf/formulation combination for about one minute, then rinsed for about 30 seconds under gently running water. After the arms were rinsed and dried at room temperature for about 5 minutes, subsequent FTIR readings were obtained throughout the day starting at 5 minutes after drying, then at 1 hour intervals until 8 hours after rinsing.

The wavelength of 1460 cm-1 at which mineral oil characteristically absorbs radiation, was monitored for all formulations. Where other oils are contained in the formulation, different wavelength bands, which correspond to the oil of interest, could alternatively be used. The amount of radiation absorbed at that wavelength was recorded for each formulation at each test interval. The results of the FTIR readings, which are shown in FIG. 1, disclosed that the formulations of Example 7 (Example 45), Example 14 (Example 47), and Example 17 (Example 46) left a measurable amount of mineral oil on the skin up to 8 hours after rinsing, which is comparable to the commercial Eucerin product (Example 48) that claims to restore moisture to the skin as it cleanses. Because the presence of residue left on the skin is an indication of moisturization, this Example further shows that the formulations of the present invention are not only effective cleansers but are also effective in depositing moisturizers, such as mineral oil, to the skin.

We claim:

1. A gelled composition comprising:
   a) a surfactant portion comprising at least one ionic surfactant;
   b) an oil;
   c) a gelling agent;
   d) a nonionic emulsifier; and
   e) no more than about 5 percent water, based upon the total weight of the composition;
   wherein (i) when the composition is applied to the skin in the presence of water the composition produces a cleansing foam; and (ii) the gelled composition has a viscosity of at least about 50,000 cps.

2. The composition of claim 1 wherein the surfactant portion is present in an amount, based upon the total weight of the composition, of from about 10 percent to about 20 percent.

3. The composition of claim 1 wherein the oil is present in an amount, based upon the total weight of the composition, from about 50 percent to about 90 percent.

4. The composition of claim 1 wherein the gelling agent is present in an amount, based upon the total weight of the composition, from about 3 percent to about 10 percent.

5. The composition of claim 1 wherein the nonionic emulsifier is present in an amount, based upon the total weight of the composition, from about 2.5 percent to about 20 percent.

6. The composition of claim 1 wherein the surfactant portion is comprised of an amphoteric surfactant, an anionic surfactant, a nonionic surfactant or a mixture thereof.

7. The composition of claim 6 wherein the amphoteric surfactant is selected from amphocarboxylates; alkyl betaines, wherein the fatty alkyl group has from about 12 carbon atoms to about 18 carbon atoms; amidoalkyl betaines wherein the fatty alkyl group has from about 12 carbon atoms to about 18 carbon atoms, and preferably from about 12 carbon atoms to about 14 carbon atoms; amidoalkyl sultaines wherein the fatty alkyl group has from about 12 carbon atoms to about 18 carbon atoms; amphophosphates; phosphobetaines; pyrophosphobetaines; carboxyalkyl alkyl polyamines wherein the first alkyl group of the carboxyalky moiety has from about 1 carbon atom to about 2 carbon atoms, and the second alkyl group has from about 12 carbon atoms to about 18 carbon atoms and mixtures thereof.

8. The composition of claim 7 wherein the amphoteric surfactant is selected from the group consisting of disodium lauroamphodiacetate, sodium lauroampho PG-acetate phosphate, cocamidopropylphosphobetaine, lauric/myristic pyrophosphobetaine, sodium carboxymethyl cocopolypropylamine, cocamidopropyl betaine, cocoamphocarboxylate, cocamidopropyl hydroxysultaine, alkyl betaines wherein the alkyl group has from about 12 carbon atoms to about 18 carbon atoms, and mixtures thereof.

9. The composition of claim 6 wherein the anionic surfactant is selected from the group consisting of alkyl sulfates; alkyl ether sulfates; alkyl monoglyceryl ether sulfates; alkyl monoglyceride sulfates; alkyl monoglyceride sulfonates; alkyl sulfonates; alkyl aryl sulfonates; alkyl sulfosuccinates; alkyl ether sulfosuccinates; alkyl sulfosuccinamates; alkyl amidosulfosuccinates; alkyl carboxylates; alkyl amidoethercarboxylates; alkyl succinates; fatty acyl sarconsinates; fatty acyl amino acids; fatty acyl taurates; fatty alkyl sulfoacetates; alkyl phosphates; and mixtures thereof, wherein the alkyl group has from about 6 carbon atoms to about 16 carbon atoms and the acyl group has from about 14 carbon atoms to about 16 carbon atoms.

10. The composition of claim 9 wherein the anionic surfactant is selected from the group consisting of sodium alkyl sulfosuccinate, wherein the alkyl group has from about 14 to about 16 carbon atoms, sodium cocoyl isethionate, cocamidopropyl MEA sulfosuccinate, sodium lauryl sulfate, and mixtures thereof.

11. The composition of claim 6 wherein the nonionic surfactants are selected from the group consisting of alkyl polyglucosides wherein the alkyl group has from about 8 carbon atoms to about 16 carbon atoms, cocoamidopropyl amine oxides, and mixtures thereof.

12. The composition of claim 6 wherein the surfactant portion contains, based upon the total weight of the surfactant portion, from about 20 percent to about 70 percent of an amphoteric surfactant and from about 20 percent to about 70 percent of an anionic surfactant.

13. The composition of claim 1 wherein the oil is a vegetable oil, a hydrocarbon oil, or mixture thereof.

14. The composition of claim 1 wherein the oil has an iodine value of less than about 80 percent.

15. The composition of claim 13 wherein the oil is a hydrocarbon oil selected from the group consisting of mineral oil; hydrogenated polyisobutylene; poly-alpha olefins wherein the olefins have from about 20 carbon atoms to about 40 carbon atoms; isododecane; isohexadecane; isoeicosane; and mixtures thereof.

16. The composition of claim 13 wherein the oil is a vegetable oil selected from the group consisting of vegetable squalane oil, coconut oil, palm kernel oil, soybean oil, macadamia nut oil, avocado oil, safflower oil, and mixtures thereof.

17. The composition of claim 1 wherein the gelling agent is dextrin myristate, dextrin palmitate, a blend of at least two different polymer members selected from the group consisting of diblock copolymers, triblock copolymers, radial block copolymers and multiblock copolymers, or a mixture thereof.

18. The composition of claim 17 wherein the blend is comprised of, based upon the total weight of the blend, from about 5 percent to about 95 percent of at least one diblock copolymer or at least one triblock copolymer, and the diblock and triblock polymers are comprised of segments of styrene monomer units and rubber monomer units.

19. The composition of claim 1 wherein the emulsifier has an HLB is less than about 10.

20. The composition of claim 1 wherein the emulsifier is selected from the group consisting of glyceryl esters; sorbitan esters; methyl glucose esters; polyethylene glycol ethers of alkyl alcohols having the formula $$CH_3(CH_2)_{10}CH_2(OCH_2CH_2)_kOH,$$

wherein k is an integer from about 1 to about 20, and preferably from about 1 to about 10, and mixtures thereof.

21. The composition of claim 20 wherein the emulsifier is selected from the group consisting of glyceryl oleate; sorbitan oleate; sorbitan stearate; methyl glucose sesquistearate; methyl glucose dioleate; polyethylene glycol ethers of alkyl alcohols having the formula $$CH_3(CH_2)_{10}CH_2(OCH_2CH_2)_kOH,$$

wherein k is an integer from about 1 to about 20, and preferably from about 1 to about 10, and mixtures thereof.

22. The composition of claim 1 further comprising a benefit agent.

23. The composition of claim 22 wherein the benefit agents is selected from the group consisting of sulfonated shale oil, elubiol, 6-(1-piperidinyl)-2,4-pyrimidinediamine-3-oxide, finasteride, ketoconazole, salicylic acid, zinc pyrithione, coal tar, benzoyl peroxide, selenium sulfide, hydrocortisone, sulfur, menthol, pramoxine hydrochloride, tricetylammonium chloride, polyquaternium 10, panthenol, panthenol triacetate, vitamin A and derivatives thereof, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, retinol, erthromycin, tretinoin, and mixtures thereof.

24. The composition of claim 22 wherein the composition contains, based upon the total weight of the composition, from about 0.001 percent to about 20 percent of the benefit agent.

25. The composition of claim 1 in the form of a personal cleansing product.

26. The composition of claim 25 wherein the personal cleansing product is in the form of a lotion, cream, gel, soap, bath, mousse, tonic, or wash.

27. The composition of claim 26 wherein the personal cleansing product is in the form of a gel.

28. A method of using the composition of claim 1 to impart a moisturizing residue to skin after the composition is rinsed therefrom.

29. A kit comprised of:
    a) the composition of claim 1; and
    b) a cleansing implement.

30. The kit of claim 29 wherein the cleansing implement is a pouf.

31. A method of treating the symptoms associated with one of the following diseases: atopic dermatitis, xerosis, psoriasis, and winter itch comprised of:
    a) topically applying an effective amount of the composition of claim 1 to a desired location on the skin.

32. The method of claim 31 further comprising rinsing the composition from the skin.

33. A method of treating dry skin comprised of:
    a) topically applying an effective amount of the composition of claim 1 to a desired location on the skin.

34. The method of claim 33 further comprising rinsing the composition from the skin.

* * * * *